(12) United States Patent
Akino et al.

(10) Patent No.: US 8,697,256 B2
(45) Date of Patent: Apr. 15, 2014

(54) COMPOSITION COMPRISING PHOSPHORESCENT COMPOUND AND LIGHT EMITTING DEVICE USING THE COMPOSITION

(75) Inventors: Nobuhiko Akino, Tsukuba (JP); Kenta Tanaka, Tsukuba (JP); Hideyuki Higashimura, Tsukuba (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 459 days.

(21) Appl. No.: 13/056,259

(22) PCT Filed: Jul. 28, 2009

(86) PCT No.: PCT/JP2009/063712
§ 371 (c)(1),
(2), (4) Date: Jan. 27, 2011

(87) PCT Pub. No.: WO2010/013827
PCT Pub. Date: Feb. 4, 2010

(65) Prior Publication Data
US 2011/0127467 A1 Jun. 2, 2011

(30) Foreign Application Priority Data
Jul. 29, 2008 (JP) ................................. 2008-194525

(51) Int. Cl.
C09K 11/06 (2006.01)
C07D 239/24 (2006.01)
H01L 51/54 (2006.01)

(52) U.S. Cl.
USPC ........... 428/690; 428/917; 313/504; 313/506; 544/242; 544/334; 252/301.16

(58) Field of Classification Search
None
See application file for complete search history.

(56) References Cited

U.S. PATENT DOCUMENTS

| | | | |
|---|---|---|---|
| 5,948,551 A | 9/1999 | Gompper et al. | |
| 2002/0028329 A1* | 3/2002 | Ise et al. | 428/336 |
| 2003/0052324 A1 | 3/2003 | Kimura | |
| 2004/0260047 A1* | 12/2004 | Chen et al. | 528/4 |
| 2005/0210672 A1 | 9/2005 | Reynolds et al. | |
| 2006/0025564 A1 | 2/2006 | Craig et al. | |
| 2006/0041126 A1 | 2/2006 | Schafer et al. | |
| 2006/0051616 A1 | 3/2006 | Suzuki et al. | |
| 2007/0099024 A1 | 5/2007 | Nii et al. | |
| 2007/0122651 A1 | 5/2007 | Igarashi | |
| 2007/0122652 A1 | 5/2007 | Hashimoto et al. | |
| 2009/0318651 A1 | 12/2009 | Tanaka et al. | |
| 2010/0019203 A1 | 1/2010 | Akino et al. | |
| 2010/0038592 A1 | 2/2010 | Akino et al. | |

FOREIGN PATENT DOCUMENTS

| | | | |
|---|---|---|---|
| JP | 07-196780 A | | 8/1995 |
| JP | H08-48972 A | | 2/1996 |
| JP | 2001-81087 A | | 3/2001 |
| JP | 2001-093670 A | * | 4/2001 |
| JP | 2002-241455 A | | 8/2002 |
| JP | 2003-045662 A | | 2/2003 |
| JP | 2004-031004 A | | 1/2004 |
| JP | 2004-095262 A | | 3/2004 |
| JP | 2004-256451 A | | 9/2004 |
| JP | 2005-089544 A | | 4/2005 |
| JP | 2006-504862 A | | 2/2006 |
| JP | 2006-76901 A | | 3/2006 |
| JP | 2008-291229 A | | 12/2008 |
| WO | 2008/081852 A1 | | 7/2008 |
| WO | 2008/096735 A1 | | 8/2008 |

OTHER PUBLICATIONS

Translation for JP 2001-093670A (publication date Apr. 2001).*
Machine-generated English translation of JP 07-196780 published Aug. 1, 1995, to Showa Denko KK.
First Office Action issued Jul. 31, 2012 in Chinese Patent Application No. 200980129482.8 to Sumitomo Chemical Company, Ltd., with English translation.
Notice of Reasons for Rejection mailed May 7, 2013 in Japanese Patent Application No. 2009-174088 with English translation.
Fang-Chung Chen et al., "High-performance polymer light-emitting diodes doped with a red phosphorescent iridium complex", Applied Physics Letters, vol. 80, No. 13, Apr. 1, 2002, pp. 2308-2310.

* cited by examiner

Primary Examiner — Dawn L. Garrett
(74) Attorney, Agent, or Firm — Sughrue Mion, PLLC

(57) ABSTRACT

A composition comprising a phosphorescent compound, and a compound having a structure containing three or more repeating units having a dipole moment dimension of 1.0 Debye or more connected in series, wherein, based on the total number of dimer structures composed of any two repeating units connected in series contained in the above-described structure, the proportion of the number of dimer structures in which the dimension $D_2$ of the dipole moment of the dimer structure, the dimension $D_{1a}$ of the dipole moment of the first repeating unit constituting the dimer structure and the dimension $D_{1b}$ of the dipole moment of the second repeating unit constituting the dimer structure satisfy a relation represented by the following formula (A):

$$D_{1a} < D_2 \text{ and } D_{1b} < D_2 \quad (A)$$

is 50% or more.

16 Claims, No Drawings

COMPOSITION COMPRISING PHOSPHORESCENT COMPOUND AND LIGHT EMITTING DEVICE USING THE COMPOSITION

CROSS REFERENCE TO RELATED APPLICATIONS

This application is a National Stage of International Application No. PCT/JP2009/063712, filed on Jul. 28, 2009, which claims priority from Japanese Patent Application No. 2008-194525, filed on Jul. 29, 2008, the contents of all of which are incorporated herein by reference in their entirety.

TECHNICAL FIELD

The present invention relates to a composition comprising a phosphorescent compound, and a light emitting device using the composition.

BACKGROUND ART

Regarding a light emitting material to be used in a light emitting layer of a light emitting device, a device using in its light emitting layer a phosphorescent compound showing light emission from the triplet excited state is known to have high luminescent efficiency. When a phosphorescent compound is used in a light emitting layer, a composition obtained by adding the compound to a matrix is usually used as a light emitting material. As the matrix, compounds such as polyfluorenes and the like are used since a film can be formed by coating with these compounds.

DISCLOSURE OF THE INVENTION

Polyfluorenes are, however, not suitable particularly for use as a matrix to light emission of shorter wavelength than green because of its small lowest triplet excitation energy (JP-A No. 2002-241455). In the case of a light emitting material composed of a polyfluorene and a triplet emitting compound (APPLIED PHYSICS LETTERS, 80, 13, 2308 (2002)), the luminescent efficiency of the resultant light emitting device is not sufficient since light emission from the triplet light emitting compound is weak.

The present invention has an object of providing a light emitting material with which the resultant light emitting device manifests excellent luminescent efficiency.

In a first aspect, the present invention provides a composition comprising a phosphorescent compound, and a compound having a structure containing three or more repeating units having a dipole moment magnitude of 1.0 Debye or more connected in series, wherein, based on the total number of dimer structures composed of any two repeating units connected in series contained in said structure, the proportion of the number of dimer structures in which the magnitude $D_2$ of the dipole moment of the dimer structure, the magnitude $D_{1a}$ of the dipole moment of the first repeating unit constituting the dimer structure and the magnitude $D_{1b}$ of the dipole moment of the second repeating unit constituting the dimer structure satisfy a relation represented by the following formula (A);

$$D_{1a} < D_2 \text{ and } D_{1b} < D_2 \quad (A)$$

is 50% or more.

In a second aspect, the present invention provides a composition comprising a phosphorescent compound and a compound having a di-valent group represented by the following formula (1-1a):

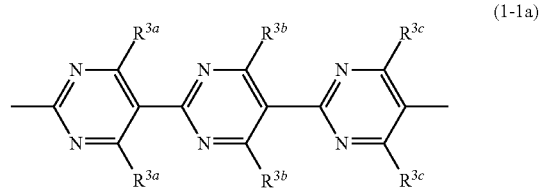

(1-1a)

[wherein $R^{3a}$, $R^{3b}$ and $R^{3c}$ represent each independently a hydrogen atom or an optionally substituted mono-valent hydrocarbon group. Two $R^{3a}$s may be the same or different, two $R^{3b}$s may be the same or different and two $R^{3c}$s may be the same or different, respectively. At least one of two $R^{3a}$s represents an optionally substituted mono-valent hydrocarbon group, at least one of two $R^{3b}$s represents an optionally substituted mono-valent hydrocarbon group and at least one of two $R^{3c}$s represents an optionally substituted mono-valent hydrocarbon group, respectively.].

In a third aspect, the present invention provides a polymer comprising a residue of a phosphorescent compound, and a residue of a compound represented by the following formula (1-1), (1-2), (2-1), (3-1) or (3-2) and having a structure containing three or more identical repeating units having a dipole moment magnitude of 1.0 Debye or more connected in series, wherein, for all dimer structures composed of any two repeating units connected in series contained in the structure, the magnitude $D_2$ of the dipole moment of the dimer structure, the magnitude $D_{1a}$ of the dipole moment of the first repeating unit constituting the dimer structure and the magnitude $D_{1b}$ of the dipole moment of the second repeating unit constituting the dimer structure satisfy the relation represented by the above-described formula (A).

In a fourth aspect, the present invention provides a compound represented by the following formula (1-1m);

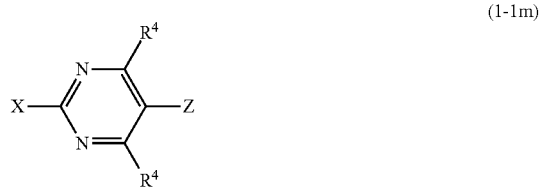

(1-1m)

[wherein X and Z represent each independently a chlorine atom, a bromine atom, an iodine atom, $CF_3SO_3$—, $CH_3SO_3$—, $C_6H_5SO_3$—, $CH_3C_6H_4SO_3$— or $B(OQ^1)_2$. $Q^1$ represents a hydrogen atom or a mono-valent hydrocarbon group, or two $Q^1$s may together form a ring. Two $Q^1$s may be the same or different. $R^4$ represents an optionally substituted mono-valent aliphatic hydrocarbon group having two or more carbon atoms. Two $R^4$s may be the same or different.].

In a fifth aspect, the present invention provides a film and a light emitting device obtained by using the above-described composition or polymer.

In a sixth aspect, the present invention provides a planar light source, a display and an illumination apparatus having the above-described light emitting device.

MODES FOR CARRYING OUT THE INVENTION

The present invention will be illustrated in detail below.
<Composition>
The composition of the present invention is a composition comprising
(1) a phosphorescent compound, and
(2) a compound having a structure containing three or more repeating units having a dipole moment magnitude of 1.0 Debye or more connected in series,
wherein, based on the total number of dimer structures composed of any two repeating units connected in series contained in the structure (for example, in the case of a structure containing repeating units $K^1$, $K^2$ and $K^3$ connected, the total number of a dimer structure of $K^1$-$K^2$ and a dimer structure of $K^2$-$K^3$ is counted as two), the proportion of the number of dimer structures in which the magnitude $D_2$ of the dipole moment of the dimer structure, the magnitude $D_{1a}$ of the dipole moment of the first repeating unit constituting the dimer structure and the magnitude $D_{1b}$ of the dipole moment of the second repeating unit constituting the dimer structure satisfy a relation represented by the following formula (A):

$$D_{1a} < D_2 \text{ and } D_{1b} < D_2 \tag{A}$$

is 50% or more.

From the standpoint of efficiently obtaining light emission from a phosphorescent compound, the composition of the present invention is preferably a composition comprising
(1) a phosphorescent compound, and
(2) a compound having a structure containing three or more repeating units having a dipole moment dimension of 1.0 Debye or more connected in series,
wherein, for all dimer structures composed of any two repeating units connected in series contained in the structure, the magnitude $D_2$ of the dipole moment of the dimer structure, the magnitude $D_{1a}$ of the dipole moment of the first repeating unit constituting the dimer structure and the magnitude $D_{1b}$ of the dipole moment of the second repeating unit constituting the dimer structure satisfy the relation represented by the above-described formula (A).

The above-described compound (2) contained in the composition of the present invention contains a partial structure having Head-to-Tail (HT) selectivity in which the orientation of a repeating unit is controlled (meaning, namely, that the orientation of a repeating unit is controlled).

In adjacent repeating units, repulsion between atoms constituting side chains optionally present on the repeating units is suppressed, which is leading to the appropriate spread of conjugation, further, also leading to a uniform certain alignment of the dipole moments of the repeating units, owing to the above-described HT selectivity, thus, a light emitting property and charge injection transportability are supposed to be excellent.

From the standpoint of a uniform certain alignment of the dipole moments of the repeating units in the above-described compound, it is preferable to satisfy a relation represented by the following formula (A-1):

$$D_{1a} < 0.8 \times D_2 \text{ and } D_{1b} < 0.8 \times D_2 \tag{A-1}$$

and it is more preferable to satisfy a relation represented by the following formula (A-2):

$$D_{1a} < 0.6 \times D_2 \text{ and } D_{1b} < 0.6 \times O_2 \tag{A-2}$$

In the composition of the present invention, the lowest triplet excitation energy ($ET_H$) of the above-described compound and the lowest triplet excitation energy ($ET_G$) of the above-described phosphorescent compound preferably satisfy a relation represented by the following formula (B'):

$$ET_H > ET_G - 0.2 \text{ (eV)} \tag{B'}$$

more preferably satisfy a relation represented by the following formula (B):

$$ET_H > ET_G \tag{B}$$

further preferably satisfy a relation represented by the following formula (B1):

$$ET_H > ET_G + 0.1 \text{ (eV)} \tag{B1}$$

and particularly preferably satisfy a relation represented by the following formula (B2):

$$ET_H > ET_G + 0.2 \text{ (eV)} \tag{B2}$$

from the standpoint of luminescent efficiency.
—Compound—
The above-described compound has a structure containing three or more repeating units connected in series, and from the standpoint of a luminescent property, and charge injection and transport properties, preferably has a structure containing five or more repeating units connected in series, more preferably has a structure containing seven or more repeating units connected in series.

In the above-described structure containing three or more repeating units connected in series, the repeating units may be composed of only one kind of unit or composed of two or more kinds of units, and from the standpoint of synthesis of the compound, preferably composed of one to three kinds of units, more preferably composed of one or two kinds of units, particularly preferably composed of only one kind of unit.

The above-described compound may be a low molecular weight compound or a polymer compound, and usually is a polymer compound. The polymer compound means a compound having a polystyrene-equivalent weight average molecular weight of $3 \times 10^2$ or more. When the above-described compound is a polymer compound, its polystyrene-equivalent weight average molecular weight is preferably $3 \times 10^2$ to $1 \times 10^7$, more preferably $1 \times 10^3$ to $1 \times 10^7$, particularly preferably $1 \times 10^4$ to $5 \times 10^6$.

In the present description, as the above-described dipole moment magnitude, a value calculated by a computational scientific method is used. Specifically, structure optimization is performed for a structure containing one repeating unit (that is, the first repeating unit singly, or the second repeating unit singly) and a structure containing two repeating units connected in series (that is, a dimer structure), using a quantum chemical calculation program MOPAC 2002 Version 1.5 (Fujitsu) by an AM1 method, and the dipole moment dimensions ($D_{1a}$, $D_{1b}$, $D_2$) in respective structures are calculated. In this procedure, calculation is performed under the proviso that each end of the above-described structures used for calculation of the dipole moment dimension is a hydrogen atom.

In the above-described compound, the above-described repeating unit is preferably a heterocyclic group containing two or more hetero atoms, more preferably a heterocyclic group containing two or more nitrogen atoms as a hetero atom. The above-described heterocyclic group may be a single ring or a condensed ring, and preferably is a single ring, more preferably a 6-membered ring. As the above-described heterocyclic group, an aromatic heterocyclic group is preferable. The above-described heterocyclic group means an atomic group remaining after removing one or more hydrogen atoms from a heterocyclic compound.

In the above-described compound, the proportion of the number of dimer structures in which the magnitude $D_2$ of the dipole moment of the above-described dimer structure, the magnitude $D_{1a}$ of the dipole moment of the first repeating unit constituting the above-described dimer structure and the magnitude $D_{1b}$ of the dipole moment of the second repeating unit constituting the above-described dimer structure satisfy the relation represented by the above-described formula (A) is preferably 50 to 100%, more preferably 60 to 100%, further preferably 80 to 100%, particularly preferably 100%, based on the total number of dimer structures composed of any two repeating units connected in series contained in the above-described structure.

For obtaining an excellent luminescent property in green to blue light emission, the lowest triplet excitation energy (hereinafter, referred to as "$T_1$ energy") of the above-described compound is preferably 2.7 eV or more, more preferably 2.9 eV or more, further preferably 3.0 eV or more, particularly preferably 3.1 eV or more, especially preferably 3.2 eV or more. Usually, the upper limit of the $T_1$ energy is 4.0 eV.

From the standpoint of electron inject property, the absolute value of the energy level of the lowest unoccupied molecular orbital (hereinafter, referred to as "LUMO") of the above-described compounds is preferably 1.5 eV or more, more preferably 1.7 eV or more, further preferably 1.9 eV or more, particularly preferably 2.0 eV or more, especially preferably 2.2 eV or more. Usually, the upper limit of the absolute value of the energy level of LUMO is 4.0 eV.

In the present description, as the $T_1$ energy and the absolute value of the energy level of LUMO, values calculated by a computational scientific method are used. In the computational scientific method, structure optimization in the ground state is performed using a quantum chemical calculation program Gaussian 03 by a HF (Hartree-Fock) method, and in the optimized structure, the $T_1$ energy and the LUMO energy are calculated using a time-dependent density functional method at B3P86 level. In this procedure, 6-31g* is used as the basis function. However, when 6-31g* cannot be used as the basis function, LANL2DZ is used.

In the above-described compound, the above-described repeating unit is preferably a repeating unit represented by a formula selected from the group consisting of the following formulae (1-1), (1-2), (1-3), (1-4), (2-1), (2-2), (2-3), (3-1), (3-2) and (3-3) (hereinafter, referred to as "the above-described formulae (1-1) to (3-3)" in some cases.).

(1-1)

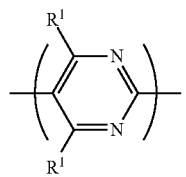

(1-2)

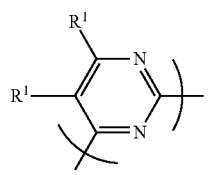

(1-3)

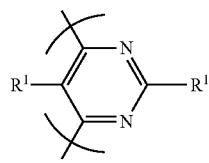

(1-4)

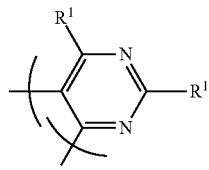

(2-1)

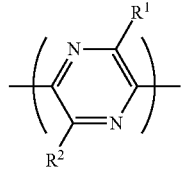

(2-2)

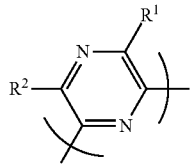

(2-3)

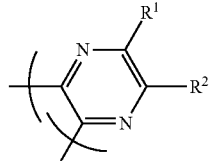

(3-1)

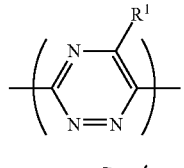

(3-2)

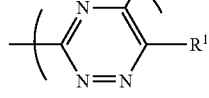

(3-3)

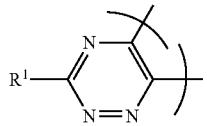

[wherein $R^1$ represents a hydrogen atom or a mono-valent group. When two $R^1$s exist, at least one of them is a mono-valent group. When two $R^1$s exist, these may be the same or different. $R^2$ represents a mono-valent group. When both $R^1$ and $R^2$ represent a mono-valent group in the formulae (2-1), (2-2) and (2-3), these represent different mono-valent groups.].

It is also preferable that the above-described repeating unit is a repeating unit represented by the following formula,

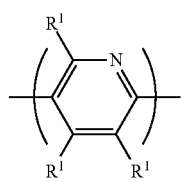 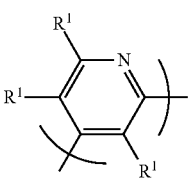

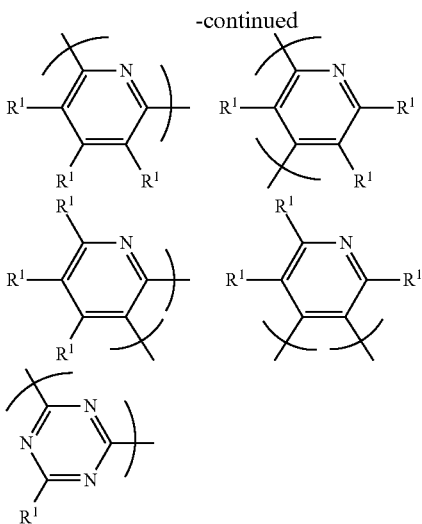

[wherein R¹ represents the same meaning as described above.].

From the standpoint of the $T_1$ energy or the LUMO energy, the above-described repeating unit is preferably a repeating unit represented by a formula selected from the group consisting of the above-described formulae (1-1), (1-2), (1-3), (1-4), (2-1), (2-2), (2-3), (3-1), (3-2) and (3-3), more preferably a repeating unit represented by a formula selected from the group consisting of the above-described formulae (1-1), (1-2), (1-3), (2-1), (2-2), (3-1) and (3-2), further preferably a repeating unit represented by a formula selected from the group consisting of the above-described formulae (1-1), (1-2), (2-1), (3-1) and (3-2).

Examples of the mono-valent group represented by $R^1$ and $R^2$ in the above-described formulae (1-1) to (3-3) include a halogen atom, an alkyl, group optionally having a substituent, an alkoxy group, an alkylthio group, an aryl group optionally having a substituent, an aryloxy group, an arylthio group, an arylalkyl group, an arylalkyloxy group, an arylalkylthio group, an acyl group, an acyloxy group, a carbamoyl group, an acid imide group, an imine residue, a substituted amino group, a substituted silyl group, a substituted silyloxy group, a substituted silylthio group, a substituted silylamino group, a mono-valent heterocyclic group optionally having a substituent, a heteroaryl group optionally having a substituent, a heteroaryloxy group, a heteroarylthio group, an arylalkenyl group, an arylethynyl group, a substituted carboxyl group and a cyano group, preferably an alkyl group optionally having a substituent, an alkoxy group, an aryl group optionally having a substituent and a heteroaryl group optionally having a substituent, more preferably an alkyl group optionally having a substituent and an aryl group optionally having a substituent, particularly preferably an alkyl group optionally having a substituent. The N-valent heterocyclic group (N is 1 or 2) is obtained by removing N hydrogen atoms from a heterocyclic compound, and the same shall apply in the present description. As the N-valent heterocyclic group, N-valent aromatic heterocyclic groups are preferable.

The carbon number of the above-described alkyl group optionally having a substituent is preferably 1 to 50, more preferably 1 to 20, further preferably 1 to 12, particularly preferably 2 to 10, especially preferably 4 to 8, from the standpoint of solubility. These carbon numbers do not include the carbon number of a substituent. Examples of the above-described alkyl group include an ethyl group, a n-propyl group, an iso-propyl group, a cyclopropyl group, a n-butyl group, an iso-butyl group, a t-butyl group, a cyclobutyl group, a pentyl group, an iso-pentyl group, a neo-pentyl group, a cyclopentyl group, a hexyl group, a cyclohexyl group, a methylcyclohexyl group, a menthyl group, a pinanyl group, a bicycloheptyl group, an octyl group, a nonyl group, a decyl group, a undecyl group and a dodecyl group.

The total number of other atoms than a hydrogen atom of the above-described mono-valent group represented by $R^1$ and $R^2$ is preferably 3 or more, more preferably 5 or more, particularly preferably 7 or more.

Use of a compound having the above-described di-valent group represented by the formula (1-1a) leads to satisfaction of all of the above-described dipole moment requirements ((A), (A-1) and (A-2)).

The optionally substituted mono-valent hydrocarbon group represented by $R^{3a}$, $R^{3b}$ and $R^{3c}$ in the above-described formula (1-1a) may be linear or cyclic. In the case of cyclic, it may be an aromatic compound group or an alicyclic compound group, and preferably, an alkyl group or an aryl group. The carbon number of the above-described alkyl group is preferably 3 or more, more preferably 4 or more, particularly preferably 6 or more.

The above-described repeating unit includes repeating units represented by the following formulae.

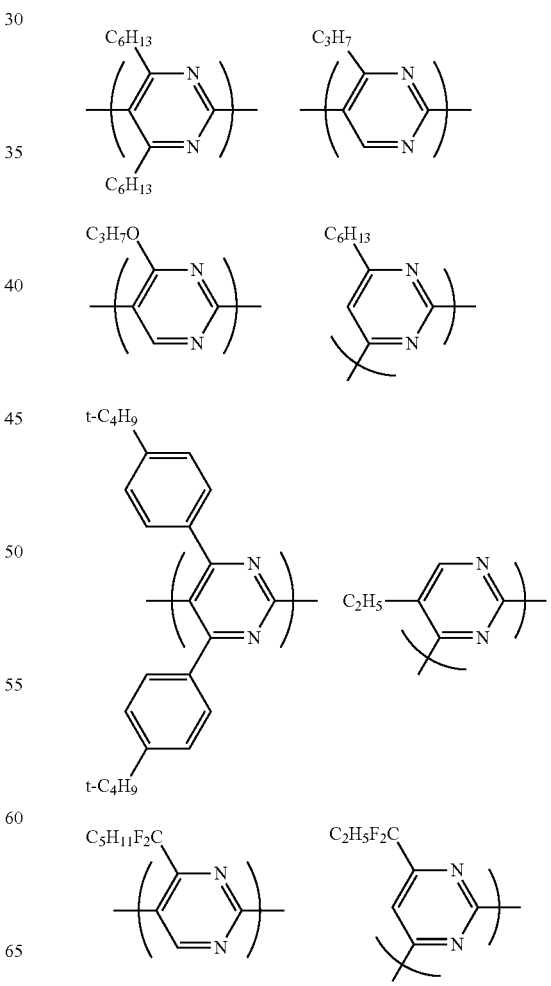

-continued

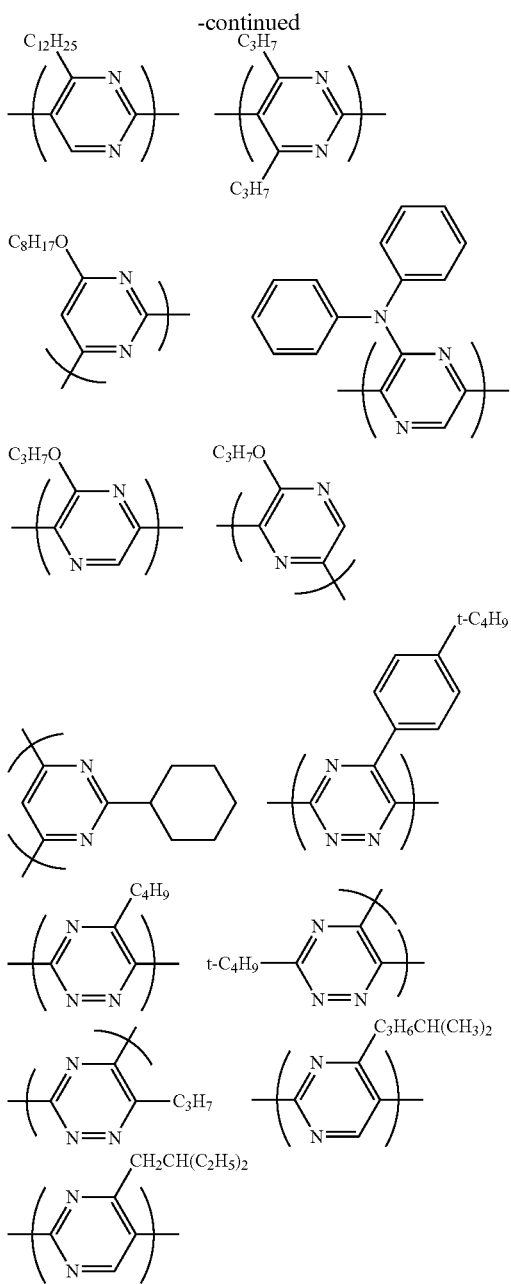

When the above-described compound is a compound having a structure containing three or more repeating units represented by any of the above-described formulae (1-1) to (3-3) connected in series, it is preferable that at least one partial structure (this partial structure has at least two π conjugated electrons) is present adjacent to the structure. The dihedral angle between the above-described structure and the partial structure adjacent to the structure is preferably 30° or more, more preferably 40° or more, further preferably 50° or more, particularly preferably 60° or more.

In the present description, the dihedral angle means a dihedral angle calculated from an optimized structure in the ground state decided by a computational scientific method. The dihedral angle is defined, for example, by a carbon atom ($a_1$) situated at a linkage position in a repeating unit represented by any of the above-described formulae (1-1) to (3-3) and a carbon atom or a nitrogen atom ($a_2$) adjacent to $a_1$, and by an atom ($a_3$) situated at a linkage position of a partial structure connected to the structure and an atom ($a_4$) adjacent to $a_3$. Here, when several atoms ($a_2$) or several atoms ($a_4$) can be selected, dihedral angles are calculated for all the cases, and the lowest absolute value (180° or less) among them is adopted as the dihedral angle. The atom ($a_3$) and the atom ($a_4$) are atoms having π conjugated electrons, preferably a carbon atom, a nitrogen atom, a silicon atom and a phosphorus atom. Ire the present description, calculation is performed from an optimized structure decided by a computational scientific method in a structure constituted of a repeating unit represented by any of the above-described formulae (I-1) to (3-3) and a partial structure connected to the unit (that is, a structure in which the heat of formation of the structure is minimum). Here, the computational scientific method is the same as the method for calculation of the $T_1$ energy and the LUMO energy, and structure optimization is performed by a HF method.

The above-described compound may have a repeating unit containing at least one structure selected from the group consisting of aromatic rings, 5- or more-membered hetero rings having a hetero atom, and a structure represented by the following formula (4):

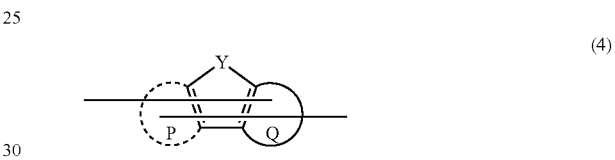

, in addition to the repeating unit represented by a formula selected from the group consisting of the above-described formulae (1-1), (1-2), (1-3), (1-4), (2-1), (2-2), (2-3), (3-1), (3-2) and (3-3).

The above-described structure represented by the formula (4) optionally has a substituent selected from the group consisting of an alkyl group, an alkoxy group, an alkylthio group, an aryl group, an alkenyl group, an alkynyl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an acyloxy group, an imine residue, a carbamoyl group, an acid imide group, a mono-valent heterocyclic group, a carboxyl group, a substituted carboxyl group and a cyano group. Preferable as this substituent are substituents selected from the group consisting of an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an acyloxy group, an imine residue, a carbamoyl group, an acid imide group, a mono-valent heterocyclic group, a carboxyl group, a substituted carboxyl group and a cyano group.

In the above-described formula (4), a ring P and a ring Q represent each independently an aromatic ring, and the ring P may not be present. When the ring P is present, two connecting bonds are present on the ring P or on the ring Q, and when the ring P is not present, two connecting bonds are present on a 5-membered or 6-membered ring containing Y or on the ring Q. The above-described ring P, ring Q and 5-membered or 6-membered ring containing Y optionally carry thereon a substituent selected from the group consisting of an alkyl group, an alkoxy group, an alkylthio group, an aryl group, an alkenyl group, an alkynyl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an acyloxy group, an imine residue, a carbamoyl group, an acid imide group, a mono-valent heterocyclic group, a carboxyl group, a substituted carboxyl group and a cyano group. Preferable as this substituent are substituents selected from the group consisting of an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an acyloxy group, an imine residue, a carbamoyl group, an acid imide group, a mono-valent heterocyclic group, a carboxyl group, a substituted carboxyl group and a cyano group. Y represents —O—, —S—, —Se—, —B(R⁰—, —Si (R²) (R³)—, —P(R⁴)—, —P(R⁵)(=O)—, —C(R⁶)(R⁷)—, —N(R⁸)—, —C(R⁹)(R¹⁰)—C(R¹¹)(R¹²)—, —O—C(R¹³)(R¹⁴)—, —S—C(R¹⁵)(R¹⁶)—, —N—C(R¹⁷)(R¹⁸)—, —Si(R¹⁹)(R²⁰)—C(R²¹)(R²²)—, —Si(R²³)(R²⁴)—Si(R²⁵)(R²⁶)—, —C(R²⁷)—C(R²⁸)—, —N=C(R²⁹)— or —Si(R³⁰)=C(R³¹)—. Here, R⁰ and R² to R³¹ represent each independently a hydrogen atom, an alkyl group, an alkoxy group, an alkylthio group, an aryl group, an alkenyl group, an alkynyl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a silyloxy group, a substituted silyloxy group, a mono-valent heterocyclic group or a halogen atom. Among them, preferable are a hydrogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a silyloxy group, a substituted silyloxy group, a mono-valent heterocyclic group and a halogen atom, more preferable are an alkyl group, an alkoxy group, an alkylthio group, an aryl group, an aryloxy group, an arylthio group, an arylalkyl group, an arylalkoxy group and a mono-valent heterocyclic group, further preferable are an alkyl group, an alkoxy group, an aryl group and a mono-valent heterocyclic group, particularly preferable are an alkyl group and an aryl group.

The above-described structure represented by the formula (4) includes structures represented by the following formula (4-1), (4-2) or (4-3):

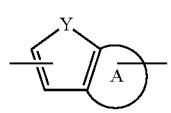

(4-1)

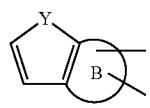

(4-2)

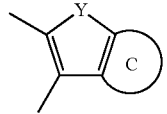

(4-3)

(wherein a ring A, a ring B and a ring C represent each independently an aromatic ring. The formulae (4-1), (4-2) and (4-3) optionally have a substituent selected from the group consisting of an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an acyloxy group, en imine residue, a carbamoyl group, an acid imide group, a mono-valent heterocyclic group, a carboxyl group, a substituted carboxyl group and a cyano group. Y represents the same meaning as described above.)

and structures represented by the following formula (4-4) or (4-5)

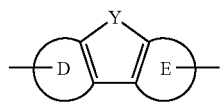

(4-4)

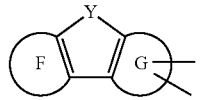

(4-5)

(wherein a ring D, a ring E, a ring F and a ring G represent each independently an aromatic ring optionally having a substituent selected from the group consisting of an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an acyloxy group, an imine residue, a carbamoyl group, an acid imide group, a mono-valent heterocyclic group, a carboxyl group, a substituted carboxyl group and a cyano group. Y represents the same meaning as described above.).

It is preferable from the standpoint of light emission efficiency that Y represents a carbon atom, a nitrogen atom, an oxygen atom or a sulfur atom in the above-described formulae (4-4) and (4-5).

The aromatic ring represented by the ring A, the ring B, the ring C, the ring D, the ring E, the ring F and the ring G in the above-described formulae (4-1), (4-2), (4-3), (4-4) and (4-5) includes aromatic hydrocarbon rings such as a benzene ring, a naphthalene ring, an anthracene ring, a tetracene ring, a pentacene ring, a pyrene ring, a phenanthrene ring and the like; and heteroaromatic rings such as a pyridine ring, a bipyridine ring, a phenanthroline ring, a quinoline ring, an isoquinoline ring, a thiophene ring, a furan ring, a pyrrole ring and the like, as examples of unsubstituted aromatic rings. These aromatic rings optionally have the above-described substituent.

The above-described compound may have a repeating unit containing an aromatic amine structure represented by the following formula:

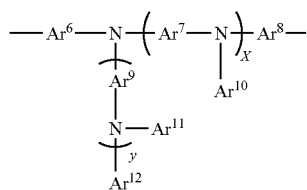

(wherein $Ar^6$, $Ar^7$, $Ar^8$ and $Ar^9$ represent each independently an arylene group or a di-valent heterocyclic group. $Ar^{10}$, $Ar^{11}$ and $Ar^{12}$ represent each independently an aryl group or a mono-valent heterocyclic group. $Ar^6$, $Ar^7$, $Ar^8$, $Ar^9$, $Ar^{10}$, $Ar^{11}$ and $Ar^{12}$ optionally have a substituent. x and y represent each independently 0 or 1, under the proviso of $0 \leq x+y \leq 1$.), in addition to the repeating unit represented by a formula selected from the group consisting of the above-described formulae (1-1), (1-2), (1-3), (1-4), (2-1), (2-2), (2-3), (3-1), (3-2) and (3-3).

The arylene group represented by $Ar^6$, $Ar^7$, $Ar^8$ and $Ar^9$ is an atomic group remaining after removing two hydrogen atoms from an aromatic hydrocarbon. The aromatic hydrocarbon includes compounds having a condensed ring, and compounds having two or more independent benzene rings or condensed rings connected directly or via a vinylene group or the like.

The di-valent heterocyclic group represented by $Ar^6$, $Ar^7$, $Ar^8$ and $Ar^9$ is an atomic group remaining after removing two hydrogen atoms from a heterocyclic compound. The di-valent heterocyclic group has a carbon atom number of usually 4 to 60. The heterocyclic compound includes organic compounds having a cyclic structure in which elements constituting the ring include not only a carbon atom but also hetero atoms such as oxygen, sulfur, nitrogen, phosphorus, boron and the like contained in the ring. As the di-valent heterocyclic group, di-valent aromatic heterocyclic groups are preferable.

The aryl group represented by $Ar^{10}$, $Ar^{11}$ and $Ar^{12}$ is an atomic group remaining after removing one hydrogen atom from an aromatic hydrocarbon. The aromatic hydrocarbon is as described above.

The mono-valent heterocyclic group represented by $Ar^{10}$, $Ar^{11}$ and $Ar^{12}$ means an atomic group remaining after removing one hydrogen atom from a heterocyclic compound. The mono-valent heterocyclic group has a carbon atom number of usually 4 to 60. The heterocyclic compound is as described above. As the mono-valent heterocyclic group, mono-valent aromatic heterocyclic groups are preferable.

The above-described compound may have another partial structure. This partial structure is preferably a poly-valent group having a conjugative nature from the standpoint of the energy of LUMO and the highest occupied molecular orbital (hereinafter, referred to as "HOMO") of the above-described compound. This group includes di-valent aromatic groups and tri-valent aromatic groups. The above-described aromatic group is a group derived from an organic compound showing an aromatic property, and examples thereof include groups obtained by substitution of n' (n' is 2 or 3) hydrogen atoms in an aromatic ring such as benzene, naphthalene, anthracene, pyridine, quinoline, isoquinoline and the like with connecting bonds.

In the above-described compound, the repeating units explained above may each be used singly or in combination of two or more.

The above-described compound includes compounds represented by the following formulae.

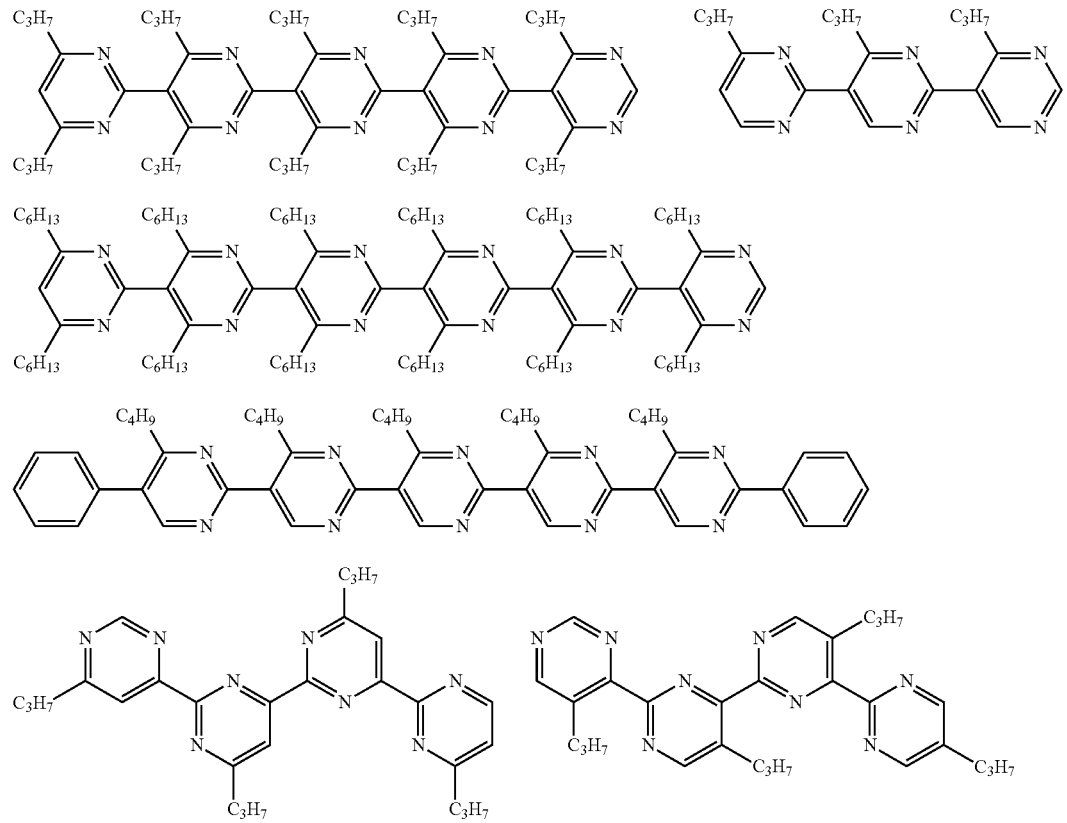

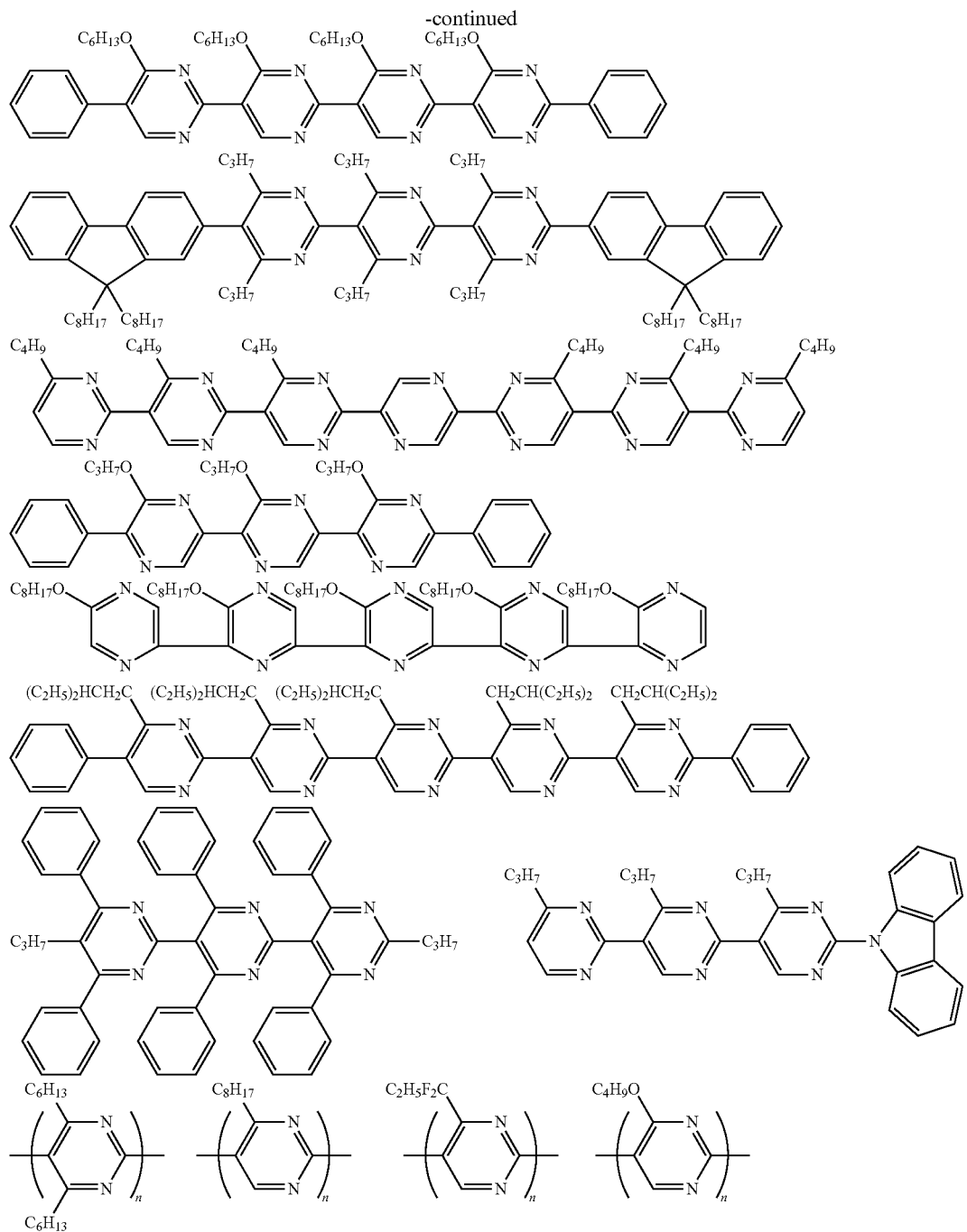

(wherein n represents degree of polymerization.).

—Compound Synthesis Method—

The above-described compound may be synthesized by any methods, and for example, can be synthesized by a method including polymerization of a compound represented by the following formula (M-1):

$$X—Ar—Z \quad (M-1)$$

[wherein, Ar is a di-valent group corresponding to the above-described repeating unit, X and Z represent each independently a chlorine atom, a bromine atom, an iodine atom, $CF_3SO_3$—, $CH_3C_6H_4SO_3$—, or $B(OQ^1)_2$. $Q^1$ represents a hydrogen atom or a mono-valent hydrocarbon group, or two $Q^1$s may together form a ring. Two $Q^1$s may be the same or different.]

in the presence of a metal catalyst.

In the above-described formula (M-1), X and Z represent preferably a chlorine atom, a bromine atom, an iodine atom or $B(OQ^1)_2$. As the combination of X and Z, combinations in which X and Z are different are preferable, and in no particular order, a combination of a chlorine atom and a bromine atom, a combination of a chlorine atom and an iodine atom, a combination of a bromine atom and an iodine atom, a combination of a bromine atom and —$B(OQ^1)_2$ and a combination of an iodine atom and —$B(OQ^1)_2$ are more preferable, and a combination of a chlorine atom and a bromine atom, a combination of a chlorine atom and an iodine atom and a combination of a bromine atom and an iodine atom are further preferable.

The above-described mono-valent hydrocarbon group represented by $Q^1$ in $-B(OQ^1)_2$ is preferably an alkyl group, more preferably a methyl group, an ethyl group, a propyl group, an isopropyl group, a butyl group, an isobutyl group, a pentyl group, a hexyl group or a nonyl group, particularly preferably a methyl group, an ethyl group, a propyl group, a butyl group, a pentyl group or a hexyl group. When two $Q^1$s together form a ring, the hydrocarbon group composed of two $Q^1$s (namely, di-valent hydrocarbon group) includes a 1,2-ethylene group, a 1,1,2,2-tetramethyl-1,2-ethylene group, a 1,3-propylene group, a 2,2-dimethyl-1,3-propylene group and a 1,2-phenylene group.

The polymerization method varies depending on the combination of X and Z. When the combination of X and Z is a combination of a chlorine atom and a bromine atom, a combination of a chlorine atom and an iodine atom or a combination of a bromine atom and an iodine atom, the Kumada coupling using a nickel complex as a metal catalyst is preferable, and in the case of a combination of a bromine atom and $-B(OQ^1)$ or a combination of an iodine atom and $-B(OQ^1)_2$, the Suzuki coupling using a palladium complex as a metal catalyst is preferable.

For synthesis of the above-described compound, compounds represented by the following formula (1-1m):

(1-1m)

[wherein X and Z represent the same meaning as described above. $R^4$ represents an optionally substituted mono-valent aliphatic hydrocarbon group having a carbon atom number of 2 or more. Two $R^4$s may be the same or different.]

are useful.

Examples of the above-described mono-valent aliphatic hydrocarbon group represented by $R^4$ in the formula (1-1m) include alkyl groups having a carbon atom number of 1 to 50 such as an ethyl group, a propyl group, an isopropyl group, a butyl group, an isobutyl group, a t-butyl group, a pentyl group, a hexyl group, a nonyl group, a dodecyl group, a pentadecyl group, an octadecyl group, a docosyl group and the like; cyclic saturated hydrocarbyl groups having a carbon atom number of 3 to 50 such as a cyclopropyl group, a cyclobutyl group, a cyclobutyl group, a cyclopentyl group, a cyclohexyl group, a cyclononyl group, a cyclododecyl group, a norbonyl group, an adamantyl group and the like; alkenyl groups having a carbon atom number of 2 to 50 such as an ethenyl group, a propenyl group, a 3-butenyl group, a 2-butenyl group, a 2-pentenyl group, a 2-hexenyl group, a 2-nonenyl group, a 2-dodecenyl group and the like; aryl groups having a carbon atom number of 6 to 50 such as a phenyl group, a 1-naphthyl group, a 2-naphthyl group, a 2-methylphenyl group, a 3-methylphenyl group, a 4-methylphenyl group, a 4-ethylphenyl group, a 4-propylphenyl group, a 4-isopropylphenyl group, a 4-butylphenyl group, a 4-t-butylphenyl group, a 4-hexylphenyl group, a 4-cyclohexylphenyl group, a 4-adamantylphenyl group, a 4-phenylphenyl group and the like; aralkyl groups having a carbon atom number of 7 to 50 such as a phenylmethyl group, a 1-phenyleneethyl group, a 2-phenylethyl group, a 1-phenyl-1-propyl group, a 1-phenyl-2-propyl group, a 2-phenyl-2-propyl group, a 3-phenyl-1-propyl group, a 4-phenyl-1-butyl group, a 5-phenyl-1-pentyl group, a 6-phenyl-1-hexyl group and the like. The mono-valent aliphatic hydrocarbon group represented by $R^4$ has a carbon atom number of preferably 2 to 20, more preferably 3 to 18, particularly preferably 3 to 13.

In the Kumada coupling, first, a compound represented by the following formula (M-2) or a compound represented by the following formula (M-3) can be synthesized by adding magnesium to the above-described compound represented by the formula (M-1) and heating the mixture, or adding an alkyl magnesium chloride such as methyl magnesium chloride, isopropyl magnesium chloride and the like to the above-described compound represented by the formula (M-1) and heating the mixture.

X—Ar—MgCl (M-2)

Z—Ar—MgCl (M-3)

(wherein X, Z and Ar represent the same meaning as described above.).

From the standpoint of obtaining more excellent light emission efficiency, one of the compound represented by the formula (M-2) and the compound represented by the formula (M-3) is produced at a ratio of preferably 4 equivalent or more, more preferably 8 equivalent or more, further preferably 12 equivalent or more, particularly preferably 16 equivalent or more, with respect to the other compound.

Next, the intended compound can be obtained by adding a suitable catalyst to the above-described compound represented by the formula (M-2) and/or the above-described compound represented by the formula (M-3). The suitable catalyst includes, for example, copper complexes, palladium complexes and nickel complexes containing ligands represented by the following formulae, among complexes described in Chem. Rev. 102, 1359 (2002).

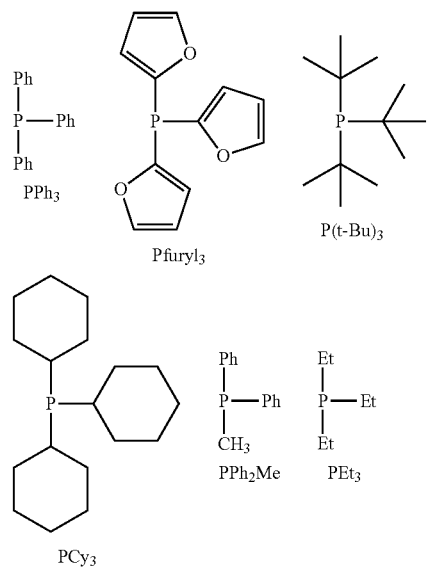

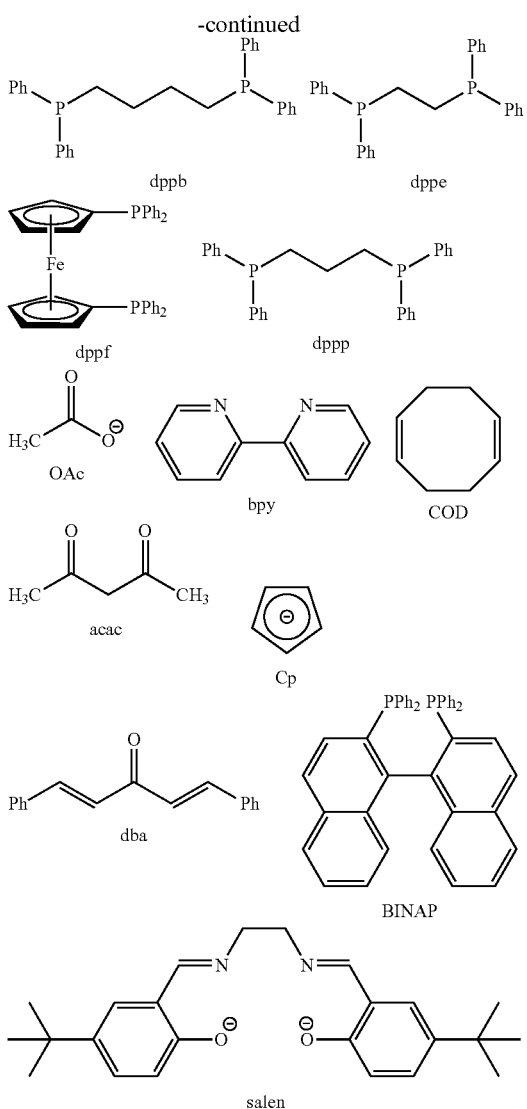

As the suitable catalyst used in the above-described polymerization reaction, Pd(PPh$_2$Me)$_2$, Pd(P(t-Bu)$_3$)$_2$, Pd(PEt$_3$)$_2$, Pd(PCy$_3$)$_2$, Pd(dppb), Pd(dppe), Pd(dppp) and Pd(BINAP) are preferable. "Ph" represents phenyl, "Me" represents methyl, "Et" represents ethyl, "t-Bu" represents tert-butyl, "Cy" represents cyclohexyl, "dppb" represents 1,4-bis(diphenylphosphino)butane, "dppe" represents 1,2-bis(diphenylphosphino)ethane, "dppp" represents 1,3-bis(diphenylphosphino)propane, and "BINAP" represents 2,2'-bis(diphenylphosphino)-1,1'-binaphthyl.

In the above-described polymerization reaction, when the above-described suitable catalyst is added in the presence of the generated metal complex, a reaction occurs between —X or —Z and —MgCl in two molecules, thereby generating a linkage between repeating units. Continuous occurrence of this reaction leads to production of the above-described compound.

Since it is considered that the selectivity (regularity) of the HT linkage in the compound obtained by the above-described polymerization reaction is determined depending on the generation selectivity of the above-described suitable catalyst and a difference between respective reactivities, it is preferable, for obtaining a compound having a sufficiently high proportion of the HT linkage, to satisfy at least one of the following conditions:

(1) only one of the compound represented by the above-described formula (M-2) and the compound represented by the above-described formula (M-3) is generated selectively, (2) there is a large difference in reactivity between the reaction of the compound represented by the above-described formula (M-2) and the reaction the compound represented by the above-described formula (M-3) under mediation of the above-described suitable catalyst.

In the above-described Suzuki coupling, the intended compound can be obtained by adding a suitable catalyst. The suitable catalyst includes copper complexes, palladium complexes, nickel complexes and the like containing the above-described ligands.

In the above-described polymerization reaction, when the above-described suitable catalyst is added in the presence of the generated organometal complex, a reaction occurs between —X and —Z in two molecules, thereby generating a linkage between the repeating units. Continuous occurrence of this reaction leads to production of the above-described compound.

As the solvent to be used in the above-described polymerization reaction, aprotic solvents and non-polar solvents scarcely causing side reactions are preferable, and examples thereof include aromatic hydrocarbons such as benzene, toluene, xylene and the like; linear and cyclic aliphatic hydrocarbons such as heptane, cyclohexane and the like; halogenated hydrocarbons such as chlorobenzene, dichlorobenzene, dichloromethane and the like; nitriles such as acetonitrile, benzonitrile and the like; ethers such as dioxane, tetrahydrofuran (hereinafter, referred to as "THF"), ethylene glycol dimethyl ether and the like; amides such as N,N-dimethylformamide, N-methylpyrrolidone and the like; nitro compounds such as nitromethane, nitrobenzene and the like. Preferable as the reaction solvent are aromatic hydrocarbons, halogenated hydrocarbons, nitriles, ethers and nitro compounds. These solvents may be used singly or in combination of two or more.

—Phosphorescent Compound—

The phosphorescent compound includes known compounds such as triplet light emitting complexes and the like, for example, compounds conventionally used as low molecular weight light emitting materials for organic EL devices. The phosphorescent compounds are disclosed in, for example, Nature, (1998), 395, 151, Appl, Phys. Lett. (1999), 75(1), 4, Proc. SPIE-Int. Soc. Opt. Eng. (2001), 4105 (Organic Light-Emitting Materials and Devices IV), 119, J. Am. Chem. Soc., (2001), 123, 4304, Appl. Phys. Lett., (1997), 71(18), 2596, Syn. Met., (1998), 94(1), 103, Syn. Met., (1999), 99(2), 1361, Adv. Mater., (1999), 11(10), 852, Inorg. Chem., (2003), 42, 8609, Inorg. Chem., (2004), 43, 6513, Journal of the SID 11/1, 161 (2003), WO2002/066552, WO2004/020504 and WO2004/020448. For the phosphorescent compound, it is preferable that, in HOMO of a metal complex, the proportion of the sum of the squares of the orbital coefficients of the outermost d-orbitals of the center metal in the sum of the squares of all atomic orbital coefficients is 1/3 or more, for obtaining high light emission efficiency, and ortho metallized complexes in which the center metal is a transition metal belonging to the VI period and the like are listed.

As the center metal of the triplet light emitting complex, usually, metals having an atomic number of 50 or more, manifesting a spin-orbital interaction to the complex, and capable of causing intersystem crossing between a singlet state and a triplet state may be advantageous, and preferable are atoms of gold, platinum, iridium, osmium, rhenium, tungsten, europium, terbium, thulium, dysprosium, samarium, praseodymium, gadolinium and ytterbium, more preferable are atoms of gold, platinum, iridium, osmium, rhenium and tungsten, further preferable are atoms of gold, platinum, iridium, osmium and rhenium, particularly preferable are atoms of gold, platinum, iridium and rhenium, especially preferable are atoms of platinum and iridium.

Examples of the ligand of the triplet light emitting complex include 8-quinolinol and derivatives thereof, benzoquinolinol and derivatives thereof, an 2-phenylpyridine and derivatives thereof.

The phosphorescent compound is preferably a compound having a substituent such as an alkyl group, an alkoxy group, an aryl group optionally having a substituent, a heteroaryl group optionally having a substituent, and the like, from the standpoint of solubility. In the substituent, the total number of other atoms than a hydrogen atom is preferably 3 or more, more preferably 5 or more, further preferably 7 or more, particularly preferably 10 or more. It is preferable that at least one substituent is present on each ligand, and the kind of the substituent may be identical or different for respective ligands.

Examples of the phosphorescent compound include the following compounds.

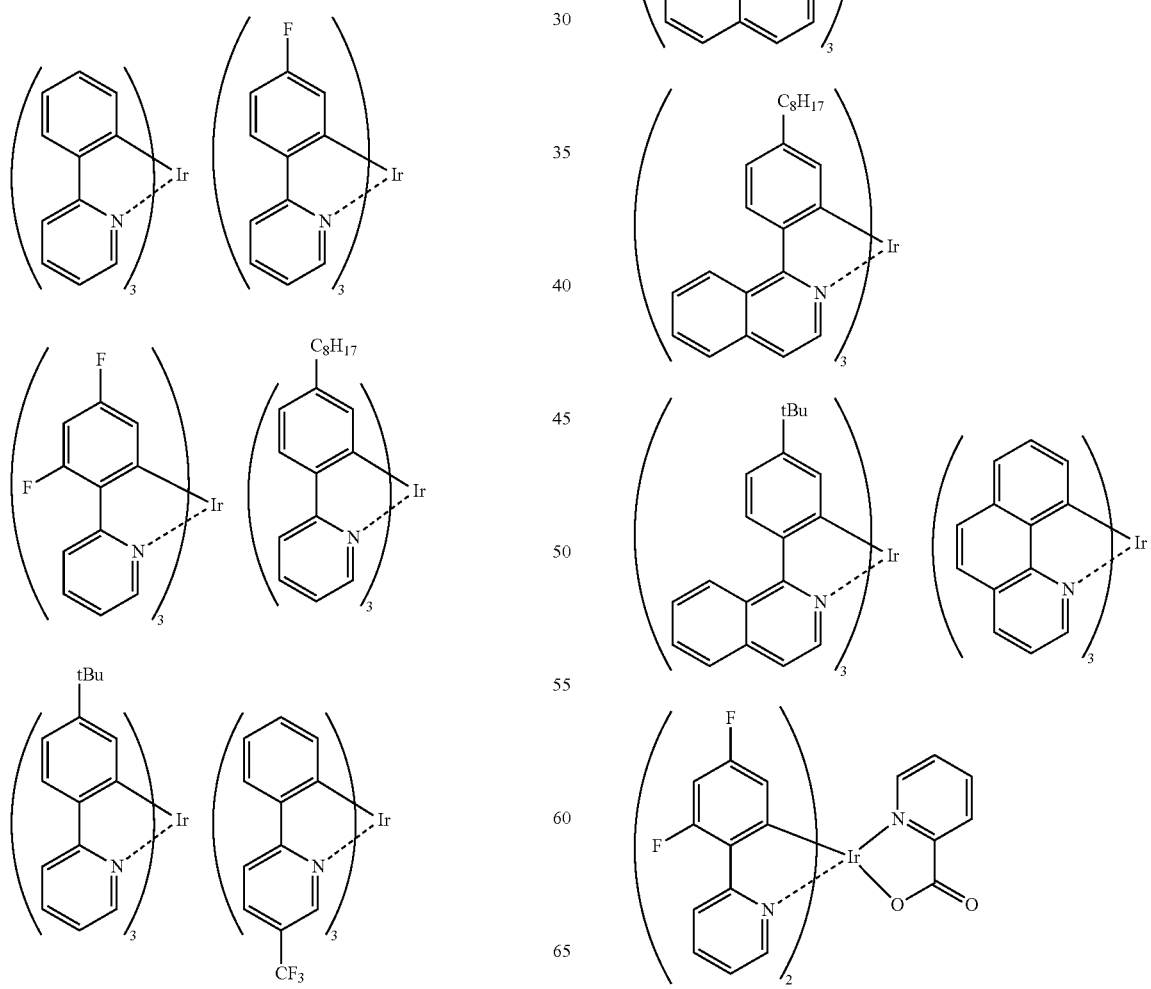

-continued

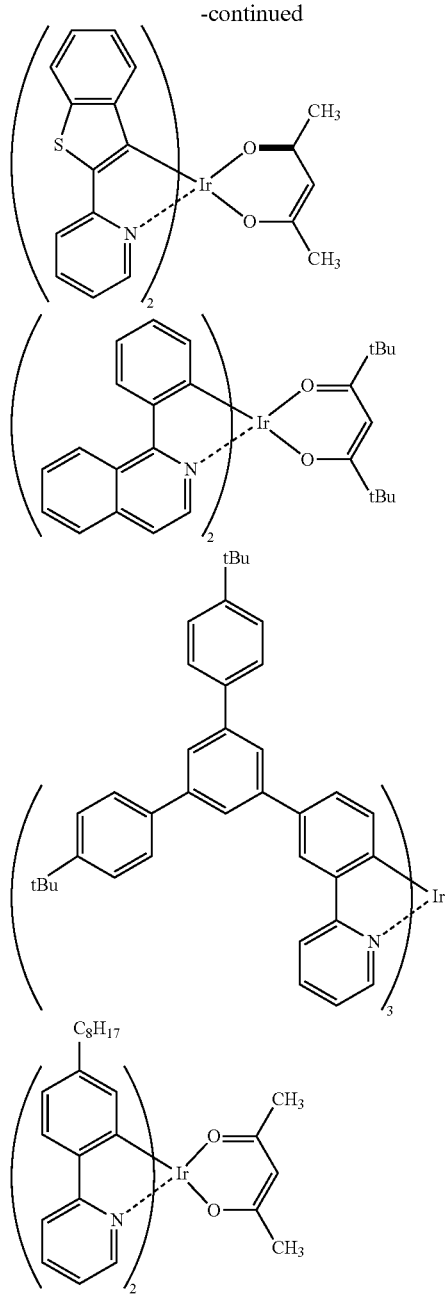

The proportion of the phosphorescent compound in the composition of the present invention is usually 0.01 to 80 parts by weight, preferably 0.1 to 30 parts by weight, more preferably 0.1 to 15 parts by weight, particularly preferably 0.1 to 10 parts by weight, if the amount of a compound having a structure containing three or more repeating units having a dipole moment dimension of 1.0 Debye or more connected in series is 100 parts by weight.

In the composition of the present invention, the above-described compound having a structure containing three or more repeating units having a dipole moment dimension of 1.0 Debye or more connected in series and the above-described phosphorescent compound may each be used singly or in combination of two or more.

The composition of the present invention may contain a hole transporting material, an electron transporting material, an antioxidant and the like, in a range not deteriorating the object of the present invention.

The above-described hole transporting material includes, for example, aromatic amines, carbazole derivatives and poly-paraphenylene derivatives known as a hole transporting material in an organic EL device.

The above-described electron transporting material includes oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, metal complexes of 8-hydroxyquinoline and derivatives thereof, known as an electron transporting material in an organic EL device.

<Polymer>

The polymer of the present invention is a polymer comprising a residue of a phosphorescent compound, and a residue of a compound represented by the above-described formulae (1-1) to (3-3), particularly, the above-described formula (1-1), (1-2), (2-1), (3-1) or (3-2) and having a structure containing identical three or more repeating units having a dipole moment dimension of 1.0 Debye or more connected in series, wherein, for all dimer structures composed of any two repeating units connected in series contained in the structure, the dimension $D_2$ of the dipole moment of the dimer structure, the dimension $D_{1a}$ of the dipole moment of the first repeating unit constituting the dimer structure and the dimension $D_{1b}$ of the dipole moment of the second repeating unit constituting the dimer structure satisfy the relation represented by the above-described formula (A). In the polymer of the present invention, the above-described residue of the phosphorescent compound may be present on any of the main chain, side chains and ends of the polymer.

<Film>

Films such as a light emitting film, an electric conductive film, an organic semiconductor film and the like can be fabricated using the composition and the polymer of the present invention (hereinafter, referred to as "composition and the like of the present invention"). For an organic semiconductor film, it is preferable that a larger parameter among electron mobility and hole mobility is $10^{-5}$ cm$^2$/V/sec or more. An organic semiconductor film can be used in an organic solar battery, an organic transistor and the like.

The film of the present invention is obtained by forming a film composed of the composition and the like of the present invention. For fabrication of the film, for example, solution coating, vapor deposition, transfer printing, and the like can be used. For solution coating, a spin coat method, a casting method, a microgravure coat method, a gravure coat method, a bar coat method, a roll coat method, a wire bar coat method, a dip coat method, a spray coat method, a screen printing method, a flexo printing method, an offset printing method, an inkjet printing method and the like may be advantageously used.

As the solvent, those capable of dissolving or uniformly dispersing the composition are preferable. Exemplified as the solvent are chlorine-based solvents (chloroform, methylene chloride, 1,2-dichloroethane, 1,1,2-trichloroethane, chlorobenzene, o-dichlorobenzene and the like), ether solvents (tetrahydrofuran, dioxane and the like), aromatic hydrocarbon solvents (toluene, xylene and the like), aliphatic hydrocarbon solvents (cyclohexane, methylcyclohexane, n-pentane, n-hexane, n-heptane, n-octane, n-nonane, n-decane and the like), ketone solvents (acetone, methyl ethyl ketone, cyclohexanone and the like), ester solvents (ethyl acetate, butyl acetate, ethylcellosolve acetate and the like), poly-hydric alcohols and derivatives thereof (ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin, 1,2-hexane diol and the like), alcohol solvents (methanol, ethanol, propanol, isopropanol, cyclohexanol and the like), sulfoxide solvents (dimethyl sulfoxide and the like), amide solvents (N-methyl-2-pyrrolidone, N,N-dimethylformamide and the like), and the solvent can be selected from them and used. These organic solvents may be used singly or in combination of two or more.

In the case of use of en inkjet printing method, known means for additives and selection of a solvent in a solution can be used for improving dischargeability from a head, fluctuation and the like. In this case, the viscosity of a solution is preferably 1 to 100 mPa·s at 25° C. If evaporation is too remarkable, repetition of discharge from a head tends to be difficult. Because of the above-described standpoint, examples of preferable solvents to be used include single or mixed solvents containing anisole, bicyclohexyl, xylene, tetralin or dodecylbenzene. In general, a solution for inkjet printing suitable for the used composition can be obtained by a method of mixing several solvents, a method of controlling the concentration of the composition in a solvent, and the like.

<Light Emitting Device>

Next, the light emitting device of the present invention will be illustrated.

The light emitting device of the present invention is obtained by using the composition or the like of the present invention, and usually, the composition or the like of the present invention is contained in at least one layer among layers disposed between electrodes consisting of an anode and a cathode, and it is preferable that this layer is a light emitting layer and the composition or the like of the present invention is contained in the form of the above-described light emitting film. From the standpoint of improving performances such as light emission efficiency, durability and the like, a layer having another function may also be contained. Examples of such a layer include charge transporting layers (namely, hole transporting layer, electron transporting layer), charge blocking layers (namely, hole blocking layer, electron blocking layer), charge injection layers (namely, hole injection layer, electron injection layer) and buffer layers. In the light emitting device of the present invention, the light emitting layer, the charge transporting layer, the charge blocking layer, the charge injection layer, the buffer layer and the like may each be composed of a single layer or two or more layers.

The light emitting layer is a layer having a function of emitting light. The hole transporting layer is a layer having a function of transporting holes. The electron transporting layer is a layer having a function of transporting electrons. These electron transporting layer and hole transporting layer are collectively called a charge transporting layer. The charge blocking layer is a layer having a function of confining holes or electrons in the light emitting layer, and a layer transporting electrons and confining holes is called a hole blocking layer, and a layer transporting holes and confining electrons is called an electron blocking layer. As the buffer layer, layers disposed adjacent to the anode and containing an electric conductive polymer are listed.

The structure of the light emitting device of the present invention includes the following structures a) to q).
a) anode/light emitting layer/cathode
b) anode/hole transporting layer/light emitting layer/cathode
c) anode/light emitting layer/electron transporting layer/cathode
d) anode/light emitting layer/hole blocking layer/cathode
e) anode/hole transporting layer/light emitting layer/electron transporting layer/cathode
f) anode/charge injection layer/light emitting layer/cathode
g) anode/light emitting layer/charge injection layer/cathode
h) anode/charge injection layer/light emitting layer/charge injection layer/cathode
i) anode/charge injection layer/hole transporting layer/light emitting layer/cathode
j) anode/hole transporting layer/light emitting layer/charge injection layer/cathode
k) anode/charge injection layer/hole transporting layer/light emitting layer/charge injection layer/cathode
l) anode/charge injection layer/light emitting layer/electron transporting layer/cathode
m) anode/light emitting layer/electron transporting layer/charge injection layer/cathode
n) anode/charge injection layer/light emitting layer/electron transporting layer/charge injection layer/cathode
o) anode/charge injection layer/hole transporting layer/light emitting layer/electron transporting layer/cathode
p) anode/hole transporting layer/light emitting layer/electron transporting layer/charge injection layer/cathode
q) anode/charge injection layer/hole transporting layer/light emitting layer/electron transporting layer/charge injection layer/cathode (Here, the mark "/" denotes adjacent lamination of layers. The same shall apply hereinafter. Two or more light emitting layers, two or more hole transporting layers, and two or more electron transporting layers may be used independently of each other.).

When the light emitting device of the present invention has a hole transporting layer (usually, a hole transporting layer contains a hale transporting material), examples of the hole transporting material include polymer hole transporting materials such as polyvinyl carbazole and derivatives thereof, polysilane and derivatives thereof, polysiloxane derivatives having an aromatic amine on a side chain or the main chain, pyrazoline derivatives, arylamine derivatives, stilbene derivatives, triphenyldiamine derivatives, polyaniline and derivatives thereof, polythiophene and derivatives thereof, polypyrrole and derivatives thereof, poly(p-phenylenevinylene) and derivatives thereof, poly(2,5-thienylenevinylene) and derivatives thereof, and the like, and further, materials described in JP-A Nos. 63-70257, 63-175860, 2-135359, 2-135361, 2-209988, 3-37992 and 3-152184 are also listed.

When the light emitting device of the present invention has an electron transporting layer (usually, an electron transporting layer contains an electron transporting material), examples of the electron transporting material include oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, metal complexes of 8-hydroxyquinoline and derivatives thereof, polyquinoline and derivatives thereof, polyquinoxaline and derivatives thereof, and polyfluorene and derivatives thereof.

The film thickness of the hole transporting layer and the electron transporting layer may advantageously be selected so as to give suitable values of driving voltage and light emission efficiency, and it is usually 1 nm to 1 μm, preferably 2 nm to 500 nm, further preferably 5 nm to 200 nm.

Among charge transporting layers disposed adjacent to an electrode, a layer having a function of improving charge injection efficiency from an electrode and having an effect of lowering the driving voltage of a device is, specifically, called a charge injection layer in some cases.

For improving close adherence to an electrode and for improving charge injection from an electrode, the above-described charge injection layer or insulation layer (usually, its average film thickness is 0.5 nm to 4 nm, the same shall apply hereinafter.) may be disposed adjacent to an electrode, and for improving close adherence to an interface and for preventing mixing, and the like, a thin buffer layer may be inserted into an interface of a charge transporting layer and a light emitting layer.

The order and the number of layers to be laminated, and the thickness of each layer can be selected in view of light emission efficiency and device life.

The charge injection layer includes a layer containing an electric conductive polymer, a layer disposed between an anode and a hole transporting layer and containing a material having ionization potential of an intermediate value between an anode material and a hole transporting material contained in the hole transporting layer, a layer disposed between a cathode and an electron transporting layer and containing a material having electron affinity of an intermediate value between a cathode material and an electron transporting material contained in the electron transporting layer, and the like.

The material used for the charge injection layer may be selected in view of a relation with the material of an electrode and an adjacent layer, and examples thereof include electric conductive polymers such as polyaniline and derivatives thereof, polythiophene and derivatives thereof, polypyrrole and derivatives thereof, polyphenylenevinylene and derivatives thereof, polythienylenevinylene and derivatives thereof, polyquinoline and derivatives thereof, polyquinoxaline and derivatives thereof, polymers containing an aromatic amine structure on the main chain or a side chain, and the like; and metal phthalocyanines (copper phthalocyanine and the like), and carbon.

The insulation layer has a function of making charge injection easy. Examples of the material of the insulation layer include metal fluorides, metal oxides and organic insulation materials. Examples of light emitting devices having the above-described insulation layer include a light emitting device having the insulation layer disposed adjacent to a cathode, and a light emitting device having the insulation layer disposed adjacent to an anode.

The light emitting device of the present invention is usually formed on a substrate. As the substrate, those which do not deform in forming an electrode and forming a layer of an organic substance are preferable, and examples thereof include substrates made of glass, plastics, polymer films, silicon and the like. In the case of an opaque substrate, it is preferable that the opposite electrode is transparent or semi-transparent.

At least one of an anode and a cathode in the light emitting device of the present invention is usually transparent or semi-transparent. Particularly, it is preferable that an anode is transparent or semi-transparent.

As the material of the anode, electric conductive metal oxide membranes, semi-transparent metal films and the like are usually used. As the material of the anode, membranes (MESA and the like) fabricated using electric conductive inorganic compounds such as indium oxide, zinc oxide, tin oxide, and composites thereof: indium.tin.oxide (ITO), indium.zinc.oxide and the like; and gold, platinum, silver, copper and the like are used, and preferable are ITO, indium.zinc-oxide and tin oxide. The anode fabrication method includes a vacuum vapor deposition method, a sputtering method, an ion plating method, a plating method and the like. For the anode, organic transparent electric conductive membranes made of polyaniline and derivatives thereof, polythiophene and derivatives thereof, and the like may be used. The anode may take a laminated structure composed of two or more layers.

As the material of the cathode, materials showing a small work function are usually preferable. As the cathode material, use is made of metals such as lithium, sodium, potassium, rubidium, cesium, beryllium, magnesium, calcium, strontium, barium, aluminum, scandium, vanadium, zinc, yttrium, indium, cerium, samarium, europium, terbium, ytterbium and the like, alloys composed of two or more of them, or alloys composed of at least one of them and at least one of gold, silver, platinum, copper, manganese, titanium, cobalt, nickel, tungsten and tin, and graphite or graphite intercalation compounds and the like. The alloy includes a magnesium-silver alloy, a magnesium-indium alloy, a magnesium-aluminum alloy, an indium-silver alloy, a lithium-aluminum alloy, a lithium-magnesium alloy, a lithium-indium alloy, a calcium-aluminum alloy, and the like. The cathode may take a laminated structure composed of two or more layers.

The light emitting device of the present invention can be used as a planar light source, a display (segment display, dot matrix display, liquid crystal display or the like), its backlight (liquid crystal display having the above-described light emitting device as backlight, and the like) or the like.

For obtaining light emission in the form of plane using the light emitting device of the present invention, it may be advantages to place a planar anode and a planar cathode so as to overlap. For obtaining light emission in the form of pattern, there are a method in which a mask having a window in the form of pattern is placed on the surface of the above-mentioned planar light emitting device, a method in which an organic layer in non-light emitting parts is formed with extremely large thickness to give substantially no light emission, a method in which either an anode or a cathode, or both electrodes are formed in the form pattern. By forming a pattern by any of these methods, and placing several electrodes so that on/off is independently possible, a display of segment type is obtained which can display digits, letters, simple marks and the like. Further, for providing a dot matrix device, it may be permissible that both an anode and a cathode are formed in the form of stripe, and placed so as to cross. By using a method in which several fluorescent bodies showing different emission colors are painted separately or a method in which a color filter or a fluorescence conversion filter is used, partial color display and multi-color display are made possible. In the case of a dot matrix device, passive driving is possible, and active driving may be carried out in combination with TFT and the like. These display devices can be used as a display of a computer, a television, a portable terminal, a cellular telephone, a car navigation, a view finder of a video camera, and the like.

The above-described planar light emitting device is usually of self emitting and thin type, and can be suitably used as a planar light source for back light of a liquid crystal display, or an illumination apparatus (for example, planar illumination, light source for the illumination), and the like. If a flexible substrate is used, it can also be used as a curved light source, illumination, display or the like.

The composition of the present invention can also be used as a semiconductor material such as an organic semiconductor material and the like, a light emitting material, an optical material, an electric conductive material (for example, applied by doping).

EXAMPLES

Examples will be shown below for illustrating the present invention further in detail, but the present invention is not limited to them.

Example 1

In a compound (C-1) represented by the following formula:

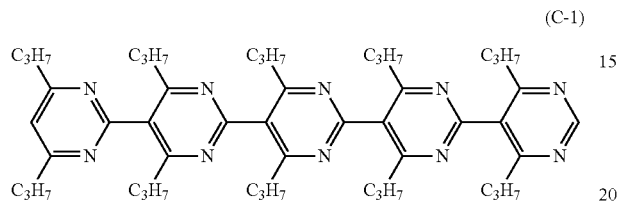

(C-1)

, a structure (C-1M) represented by the following formula:

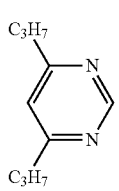

(C-1M)

in which ends of the repeating unit were composed of a hydrogen atom had a dipole moment magnitude $D_1$ ($D_{1a}$ or $D_{1b}$) of 2.3 Debye, and a dimer structure (C-1-2)(end hydrogen atom) represented by the following formula:

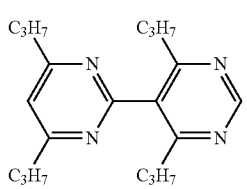

(C-1-2)

had a dipole moment dimension $D_2$ of 4.4 Debye, meaning $D_1 < D_2$. Calculation of the dipole moment was carried out according to the above-described computational scientific method. Specifically, structure optimization was performed for the above-described structure (C-1M) and the above-described dimer structure (C-1-2) in the above-described compound (C-1) by an AM1 method, and the dipole moment in the optimized structure was calculated.

The above-described compound (C-1) had a $T_1$ energy of 3.7 eV, and an absolute value of the energy level of LUMO of 2.0 eV. Calculation of the $T_1$ energy and the LUMO energy level value was performed according to the above-described computational scientific method. Specifically, structure optimization was performed for the above-described compound (C-1) by a HF method. In this procedure, 6-31G* was used as the basis function. Thereafter, the $T_1$ energy and the LUMO energy were calculated by a time-dependent density functional method of B3P86 level, using the same basis.

When a light emitting device is fabricated using a composition composed of the compound (C-1) and a phosphorescent compound, excellent light emission efficiency can be confirmed.

Example 2

In a compound (C-2) represented by the following formula:

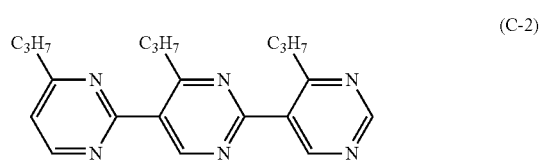

(C-2)

, a structure (C-2M) represented by the following formula:

(C-2M)

in which ends of the repeating unit were composed of a hydrogen atom had a dipole moment magnitude $D_1$ ($D_{1a}$ or $D_{1b}$) of 2.2 Debye, and a dimer structure (C-2-2)(end hydrogen atom) represented by the following formula:

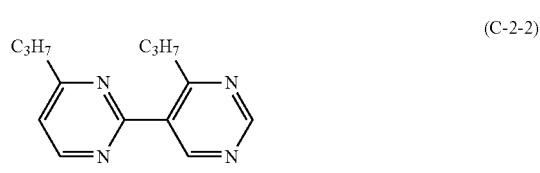

(C-2-2)

had a dipole moment magnitude $D_2$ of 4.3 Debye, meaning $D_1 < D_2$.

The above-described compound (0-2) had a $T_1$ energy of 3.2 eV, and an absolute value of the energy level of LUMO of 2.6 eV.

The dipole moment, the $T_1$ energy and the LUMO energy value were calculated in the same manner as in Example 1.

When a light emitting device is fabricated using a composition composed of the above-described compound (C-2) and a phosphorescent compound, excellent light emission efficiency can be confirmed.

Example 3

Synthesis of pentadecane-7,9-dione

Lithium amide (12.4 g, 498 mmol) was dissolved in 130 mL of methyl t-butyl ether (MTBE), and a solution of 32.4 g (253 mmol) of octan-2-one in MTBE (67 mL) was dropped under a nitrogen atmosphere at 35° C. and the mixture was stirred for 1 hour. Then, into this was dropped a solution of 80.0 g (506 mmol) of ethyl pentanoate in MTBE (67 mL), and the mixture was stirred at 35° C. for 4.5 hours. After cooling, the resultant mixed liquid was added into concentrated hydrochloric acid containing ice added, and the oil phase was extracted and died over sodium sulfate, then, concentrated.

For purification of the resultant concentrate, a copper acetate aqueous solution was added to cause crystallization of a copper complex of the concentrate, which was dissolved in MTBE and mixed with a sulfuric acid aqueous solution and the mixture was returned to the concentrate, and the oil phase was extracted and dried over sodium sulfate and concentrated, to obtain 36.3 g (151 mmol) of pentadecane-7,9-dione.

Synthesis of 4,6-dihexylpyrimidin-2-ol

Pentadecane-7,9-dione (60.0 g, 250 mmol) and 30 g (500 mmol) of urea were dissolved in 3750 mL of ethanol, and under a nitrogen atmosphere, 75 mL of concentrated hydrochloric acid was added, and the mixture was gradually heated until reflux, and allowed to reflux for 18.5 hours. After cooling down to room temperature, water and ethyl acetate were added, the oil phase was extracted, and washed with a saturated sodium bicarbonate solution and saturated saline in this order, and dried over magnesium sulfate and concentrated. The resultant concentrate was purified by a silica gel column (hexane•ethyl acetate) to obtain 31.2 g of 4,6-dihexylpyrimidin-2-ol.

Synthesis of 5-bromo-4,6-dihexylpyrimidin-2-ol 4,6-dihexylpyrimidin-2-ol (31.2 g, 118 mmol) was dissolved in 375 mL of dimethylformamide, and 21.0 g (118 mmol) of N-bromo-succinimide was added at 3° C., and the mixture was stirred for 2.5 hours. Ice water (500 g) was added, and the mixture was extracted with ethyl acetate, washed with saturated saline, dried over magnesium sulfate and concentrated. The concentrate was purified by re-crystallization from ethanol, and the purity thereof was enhanced by a silica gel column (hexane•ethyl acetate) to obtain 8.4 g (24 mmol) of 5-bromo-4,6-dihexylpyrimidin-2-ol.

Synthesis of 5-bromo-2-chloro-4,6-dihexylpyrimidine

To 19.6 g (57.1 mmol) of 5-bromo-4,6-dihexylpyrimidin-2-ol was added 2.8 g (23 mmol) of N,N-dimethylaniline, and 40.8 g (266 mmol) of phosphoryl chloride was added under a nitrogen atmosphere, and the mixture was stirred at 100° C. for 2 hours. The resultant mixed liquid was cooled down to room temperature, then, 200 g of ice water was added, and the mixture was extracted with MTBE, washed with water and saturated saline in this order, dried over magnesium sulfate and concentrated. The resultant concentrate was purified by a silica gel column (hexane•ethyl acetate) to obtain 20.5 g (56.7 mmol) of 5-bromo-2-chloro-4,6-dihexylpyrimidine represented by the following formula:

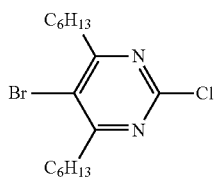

Synthesis Example

Under an argon atmosphere, 308 mg (0.851 mmol) of 5-bromo-2-chloro-4,6-dihexylpyrimidine was dissolved in 3 ml of dehydrated THF, the solution was cooled down to 0° C., then, 0.46 ml (0.92 mmol) of a 2.0M isopropyl magnesium chloride THF solution was dropped, and the mixture was stirred for 2 hours. To this was additionally added 0.18 ml (0.36 mmol) of a 2.0M isopropyl magnesium chloride THF solution and the mixture was stirred for 1 hour, then, a suspension of 8.9 mg (0.025 mmol) of nickel(II) acetylacetonate and 10.4 mg (0.030 mmol) of 1,3-bis(2,4,6-trimethylphenyl) imidazolium chloride in 3 ml of dehydrated THF was added and the mixture was heated up to 60° C. and stirred for 16 hours. The resultant mixed liquid was cooled, and 1 ml of distilled water was added, then, the mixture was filtered. The resultant precipitate was washed with distilled water and THF in this order, and the precipitate was dried under reduced pressure, to obtain 34.2 mg (yield: 16.8%) of HT regioregular poly(4,6-dihexylpyrimidine-2,5-diyl) in the form of a dark brownish powder.

$^1$H-NMR of the resultant HT regioregular poly(4,6-dihexylpyrimidine-2,5-diyl) in a mixed liquid of deuterated chloroform:trifluoroacetic acid (volume ratio=1:1) was measured. A spectrum consistent with the HT structure could be obtained. Peaks were observed at an interval of the mass of the repeating unit, by MALDI-TOFMS measurement.

In the repeating unit of thus obtained HT regioregular poly(4,6-dihexylpyrimidine), a structure (D-7) represented by the following formula:

in which ends of the unit were composed of a hydrogen had a dipole moment size $D_1$ ($D_{1a}$ or $D_{1b}$) of 2.2 Debye, and a dimer structure (D-7-2) represented by the following formula:

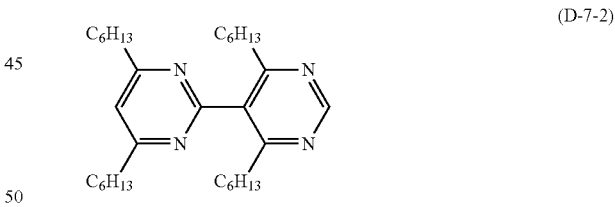

had a dipole moment dimension $D_2$ of 4.3 Debye, meaning $D_1 < D_2$.

Reference Example

Under an argon atmosphere, 301 mg (0.831 mmol) of 5-bromo-2-chloro-4,6-dihexylpyrimidine was dissolved in 3 ml of dehydrated THF, the solution was cooled down to 0° C., then, 0.41 ml (0.82 mmol) of a 2.0M isopropyl magnesium chloride THF solution was dropped and the mixture was stirred for 70 minutes. The mass spectrum of the resultant mixed liquid was measured. As a result, a peak ascribable to 5-bromo-2-chloro-4,6-dihexylpyrimidine, and a peak ascribable to a compound (D-3) represented by the following formula:

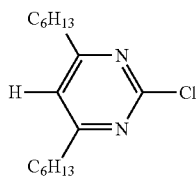 (D-3)

generated by reaction of moisture in air with a compound (D-2) represented by the following formula:

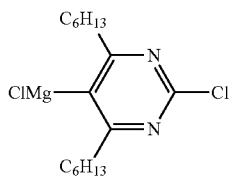 (D-2)

generated by reaction of 5-bromo-2-chloro-4,6-dihexylpyrimidine with isopropyl magnesium chloride were recognized, however, a peak ascribable to a compound (D-5) represented by the following formula:

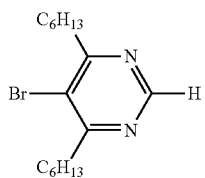 (D-5)

generated by reaction of moisture in air with a compound (D-4) represented by the following formula:

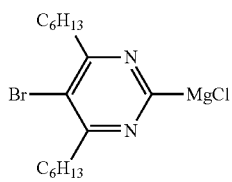 (D-4)

which was a by-product for the above-described compound (D-2) was not recognized. Based on this fact, it was confirmed that the above-described compound (D-2) was generated quantitatively from 5-bromo-2-chloro-4,6-dihexylpyrimidine. That is, it was confirmed that, also in a synthesis example under approximately the same conditions, the above-described compound (D-2) was generated quantitatively from 5-bromo-2-chloro-4,6-dihexylpyrimidine, and by addition of nickel(II) acetylacetonate and 1,3-bis(2,4,6-trimethylphenyl)imidazolium chloride, coupling occurred at a ClMg site and a Cl site of the compound (D-2), to cause quantitative generation of a polymer compound having a structure (D-6) represented by the following formula:

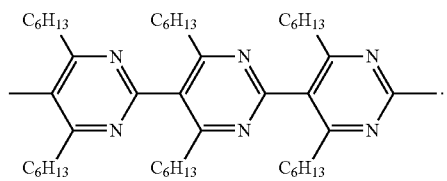 (D-6)

Therefore, it was shown that the compound (poly(4,6-dihexylpyrimidine-2,5-diyl)) synthesized in Example 3 was HT regioregular.

Example 4

A THF solution (0.05 wt %) of a phosphorescent compound (MC-1) represented by the following formula:

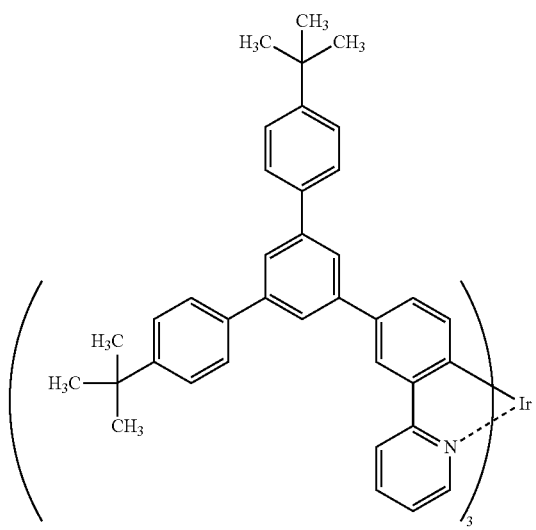 (MC-1)

was mixed with a THF solution (approximately 1 wt %) of the HT regioregular poly(4,6-dihexylpyrimidine) obtained in Synthesis Example of approximately 5-fold weight, to obtain a solution of a mixture. The resultant solution (10 μl) was dropped onto a slide glass, and dried in air to obtain a solid membrane. This was irradiated with 365 nm ultraviolet ray, to observe intense green light emission from the phosphorescent compound (MC-1), thus, high light emission efficiency of the above-described mixture was recognized.

The above-described phosphorescent compound (MC-1) was synthesized according to a method described in WO 02/066552.

Example 5

A solution was prepared in the same manner as in Example 4 excepting that a phosphorescent compound (MC-2, manufactured by American Dye Source Inc., trade name: ADS065BE) represented by the following formula;

(MC-2)

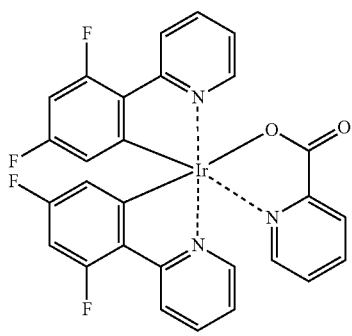

was used instead of the above-described phosphorescent compound (MC-1) in Example 4, and irradiated with 254 nm ultraviolet ray, to observe intense water blue light emission from the above-described phosphorescent compound (MC-2), thus, high luminescent efficiency of the above-described compound was confirmed.

Industrial Applicability

With the composition and the polymer of the present invention, the resultant light emitting device shows high light emission efficiency. The composition or the like of the present invention usually shows a relatively excellent light emitting property in green to blue light emission, since the compound contained in the composition of the present invention and the polymer of the present invention have large lowest triple excitation energy. Also the energy level of the lowest unoccupied molecular orbital (LUMO) is relatively low, and electrons can be injected easily.

The invention claimed is:

1. A composition comprising a phosphorescent emitting compound, and a compound having a structure containing three or more repeating units having a magnitude of dipole moment of 1.0 Debye or more connected in series,
wherein, based on the total number of dimer structures composed of any two repeating units connected in series contained in said structure, the proportion of the number of dimer structures in which the magnitude $D_2$ of the dipole moment of the dimer structure, the magnitude $D_{1a}$ of the dipole moment of the first repeating unit constituting the dimer structure and the magnitude $D_{1b}$ of the dipole moment of the second repeating unit constituting the dimer structure satisfy a relation represented by the following formula (A):

$$D_{1a} < D_2 \text{ and } D_{1b} < D_2 \quad (A)$$

is 50% or more,
wherein said repeating unit is a repeating unit represented by a formula selected from the group consisting of the following formulae (1-1), (1-2), (1-3), (1-4), (2-1), (2-2), (2-3), (3-1), (3-2) and (3-3):

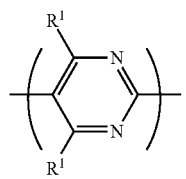
(1-1)

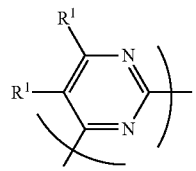
(1-2)

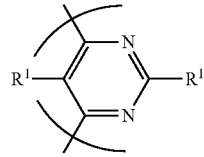
(1-3)

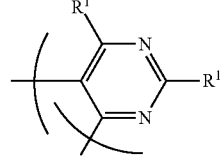
(1-4)

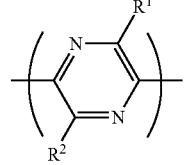
(2-1)

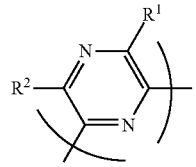
(2-2)

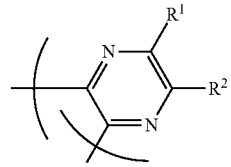
(2-3)

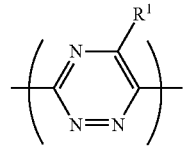
(3-1)

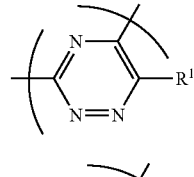
(3-2)

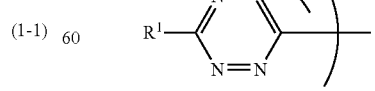
(3-3)

wherein $R^1$ represents a hydrogen atom or a mono-valent group, when two $R^1$s exist, at least one of them is a mono-valent group, when two $R^1$s exist, these may be the same or different, $R^2$ represents a mono-valent group, and when both $R^1$ and $R^2$ represent a mono-valent group in the formulae (2-1), (2-2) and (2-3), these represent different mono-valent groups.

2. The composition according to claim 1 comprising a phosphorescent emitting compound, and a compound having a structure containing three or more repeating units having a dipole moment magnitude of 1.0 Debye or more connected in series, wherein, for all dimer structures composed of any two repeating units connected in series contained in said structure, the magnitude $D_2$ of the dipole moment of the dimer structure, the magnitude $D_{1a}$ of the dipole moment of the first repeating unit constituting the dimer structure and the magnitude $D_{1b}$ of the dipole moment of the second repeating unit constituting the dimer structure satisfy the relation represented by said formula (A).

3. The composition according to claim 1 wherein the lowest triplet excitation energy ($ET_H$) of said compound and the lowest triplet excitation energy ($ET_G$) of said phosphorescent emitting compound satisfy a relation represented by the following formula (B'):

$$ET_H > ET_G - 0.2 \text{ (eV)} \tag{B'}$$

4. The composition according to claim 1 wherein the lowest triplet excitation energy ($ET_H$) of said compound and the lowest triplet excitation energy ($ET_G$) of said phosphorescent emitting compound satisfy a relation represented by the following formula (B):

$$ET_H > ET_G \tag{B}$$

5. The composition according claim 1 wherein the lowest triplet excitation energy of said compound is 2.7 eV or more.

6. The composition according to claim 1 wherein the absolute value of the energy level of the lowest unoccupied molecular orbital of said compound is 1.5 eV or more.

7. The composition according to claim 1 comprising a phosphorescent emitting compound, and a compound represented by a formula selected from the group consisting of said formulae (1-1), (1-2), (2-1), (3-1) and (3-2) and having a structure containing three or more repeating units having a dipole moment magnitude of 1.0 Debye or more connected in series, wherein, for all dimer structures composed of any two repeating units connected in series contained in said structure, the magnitude $D_2$ of the dipole moment of the dimer structure, the magnitude $D_{1a}$ of the dipole moment of the first repeating unit constituting the dimer structure and the magnitude $D_{1b}$ of the dipole moment of the second repeating unit constituting the dimer structure satisfy the relation represented by said formula (A).

8. A composition comprising a phosphorescent emitting compound and a compound having a di-valent group represented by the following formula (1-1a):

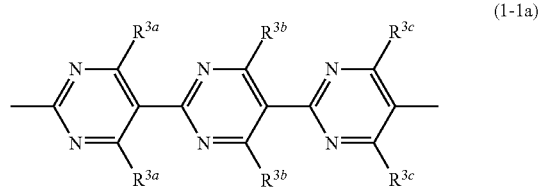

(1-1a)

wherein $R^{3a}$, $R^{3b}$ and $R^{3c}$ represent each independently a hydrogen atom or an optionally substituted mono-valent hydrocarbon group, two $R^{3a}$s may be the same or different, two $R^{3b}$s may be the same or different and two $R^{3c}$s may be the same or different, respectively, at least one of two $R^{3a}$s represents an optionally substituted mono-valent hydrocarbon group, at least one of two $R^{3b}$s represents an optionally substituted mono-valent hydrocarbon group and at least one of two $R^{3c}$s represents an optionally substituted mono-valent hydrocarbon group, respectively.

9. A polymer comprising a residue of a phosphorescent emitting compound, and a residue of a compound having a structure containing identical three or more repeating units having a dipole moment magnitude of 1.0 Debye or more connected in series represented by the following formula (1-1), (1-2), (2-1), (3-1) or (3-2):

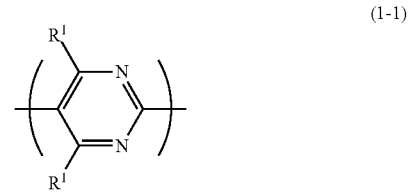

(1-1)

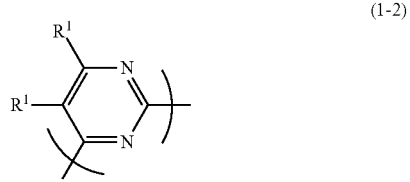

(1-2)

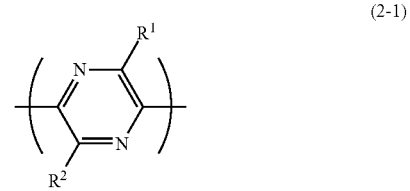

(2-1)

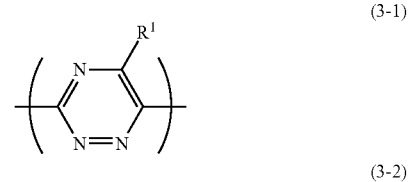

(3-1)

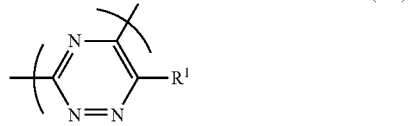

(3-2)

wherein $R^1$ represents a hydrogen atom or a mono-valent group, when two $R^1$s exist, at least one of them is a mono-valent group, when two $R^1$s exist, these may be the same or different, wherein, for all dimer structures composed of any two repeating units connected in series contained in said structure, the magnitude $D_2$ of the dipole moment of the dimer structure, the magnitude $D_{1a}$ of the dipole moment of the first repeating unit constituting the dimer structure and the magnitude $D_{1b}$ of the dipole moment of the second repeating unit constituting the dimer structure satisfy the relation represented by the following formula (A):

$$D_{1a} < D_2 \text{ and } D_{1b} < D_2 \tag{A}$$

10. A film comprising the composition according to claim 1.

11. A light emitting device comprising the composition according to claim 1.

12. A planar light source comprising the light emitting device according to claim 11.

13. A display comprising the light emitting device according to claim 11.

14. An illumination apparatus comprising the light emitting device according to claim 11.

15. A film comprising the polymer according to claim 9.

16. A light emitting device comprising the polymer according to claim 9.

\* \* \* \* \*